(12) United States Patent
Ushida et al.

(10) Patent No.: US 7,582,305 B2
(45) Date of Patent: Sep. 1, 2009

(54) ANTIDIARRHEAL AGENT FOR LIVESTOCK AND POULTRY

(75) Inventors: Kazunari Ushida, Nishinomiya (JP); Takamitsu Tsukahara, Kawanishi (JP); Wakoto Bukawa, Saitama (JP); Tatsuhiko Kan, Sayama (JP); Takumi Watanabe, Saitama (JP); Noritaka Matsubara, Saitama (JP)

(73) Assignee: Combi Co., Tokyo (JP)

( * ) Notice: Subject to any disclaimer, the term of this patent is extended or adjusted under 35 U.S.C. 154(b) by 222 days.

(21) Appl. No.: 11/522,161

(22) Filed: Sep. 15, 2006

(65) Prior Publication Data

US 2007/0065423 A1 Mar. 22, 2007

Related U.S. Application Data

(63) Continuation-in-part of application No. PCT/JP2005/004572, filed on Mar. 15, 2005.

(30) Foreign Application Priority Data

Mar. 16, 2004 (JP) ............................. 2004-075429

(51) Int. Cl.
*A61K 39/02* (2006.01)
*A61K 39/00* (2006.01)
*A01K 63/00* (2006.01)

(52) U.S. Cl. .................................. 424/234.1; 424/93.4
(58) Field of Classification Search .................. None
See application file for complete search history.

(56) References Cited

U.S. PATENT DOCUMENTS 5,698,437 A * 12/1997 Matsuda et al. ............. 435/244
6,333,188 B1 * 12/2001 Hata et al. ................ 435/252.4
2008/0206380 A1 8/2008 Ushida et al.

FOREIGN PATENT DOCUMENTS

JP 2004-41099 2/2004
JP 2004-51530 2/2004

OTHER PUBLICATIONS

Bukawa, et al. Infection Protective Activities of Sterilized Lactic Acid "EC-12" and Agaricus, Food Style 21 6(9): 73-76, 2002.
Yuichiro Kuramoto, et al., Effects of Heat-killed Bacterial Component Derived from Enterococcus Faecalis on Biological Defense Systems, The Japanese Society for Immunology Gakujutsu Shukai Kiroku 32: 132, 2002.
Yuichiro Kuramoto, et al., Effects of Heat-killed Bacterial Component Derived from Enterococcus Faecalis On Biological Defense Systems, Biotherapy 16:107, 2002.
Yuichiro Kuramoto, et al., Effects of Heat-killed EC-12 Derived from lactic Acid Bacteria on Biological Defense Systems, Shin'yaku to Rinsho 53(3): 298-308, 2004.
Atsushi Terada, et al., Effects of the Consumption of Heat-killed Enterococcus Faecalis EC-12 Preparation on Microbiota and Metabolic Activity of the Faeces in Healthy Adults, Microbial Ecology in Health and Disease (2004) vol. 16, p. 188-194.

* cited by examiner

*Primary Examiner*—Vera Afremova
(74) *Attorney, Agent, or Firm*—Fromer Lawrence & Haug LLP; Thomas J. Kowalski; Smitha B. Uthaman

(57) ABSTRACT

The present invention is to provide a safe antidiarrheal agent and a method for suppressing diarrhea by which an efficient antidiarrheal effect is achieved without using antibiotics or synthetic antibacterial agents that have been conventionally used against infections in livestock and poultry. Antibiotic-resistant pathogenic infections can also be prevented and treated by the present invention. The antidiarrheal agent for livestock and poultry comprising heat-killed bacteria of *Enterococcus faecalis* EC-12 (FERM ABP-10284) or a treated product thereof as an active ingredient is orally administered to livestock and poultry, particularly to breast-feeding sows and piglets around the weaning period.

6 Claims, 3 Drawing Sheets

[Fig. 1]
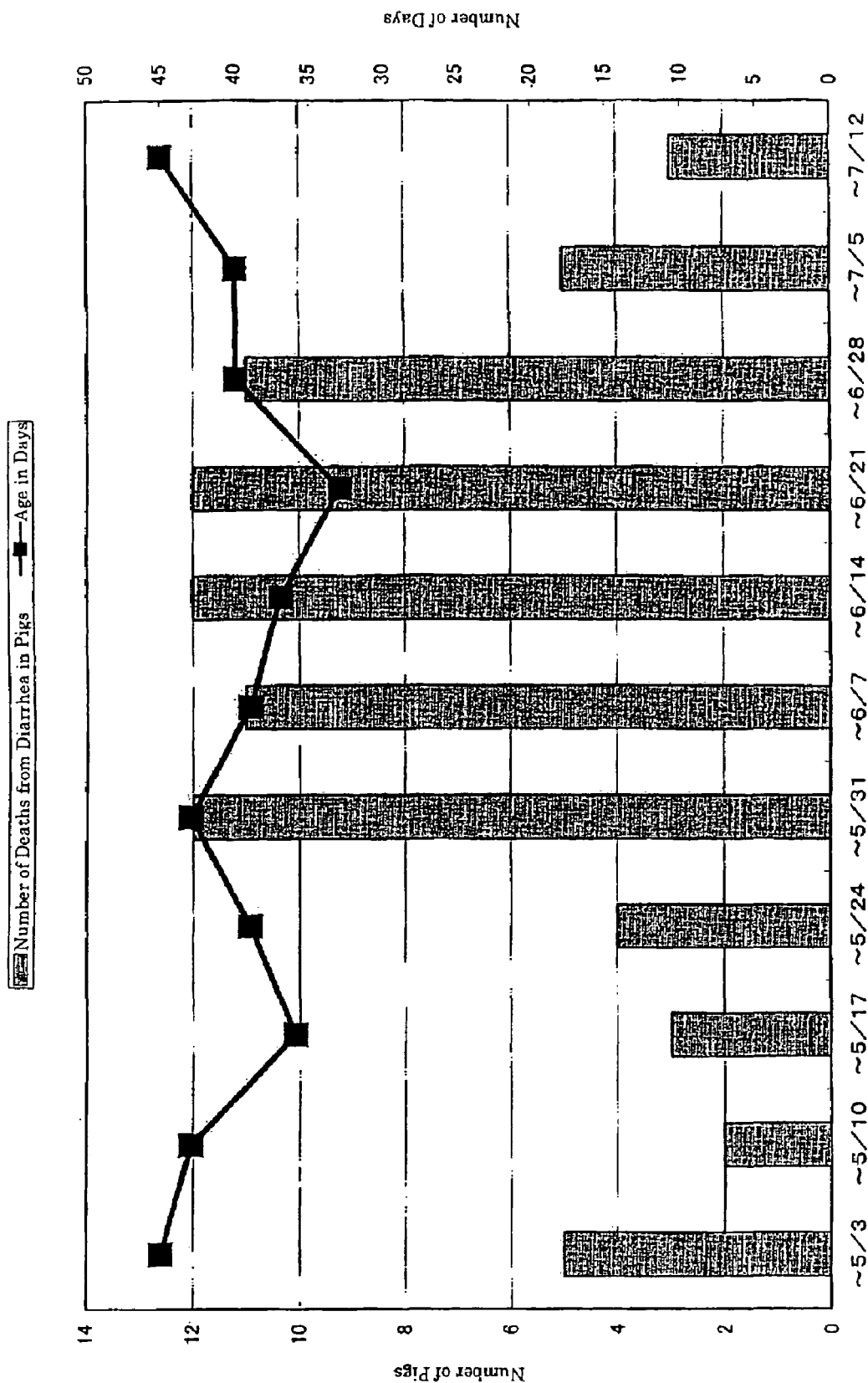

[Fig. 2]
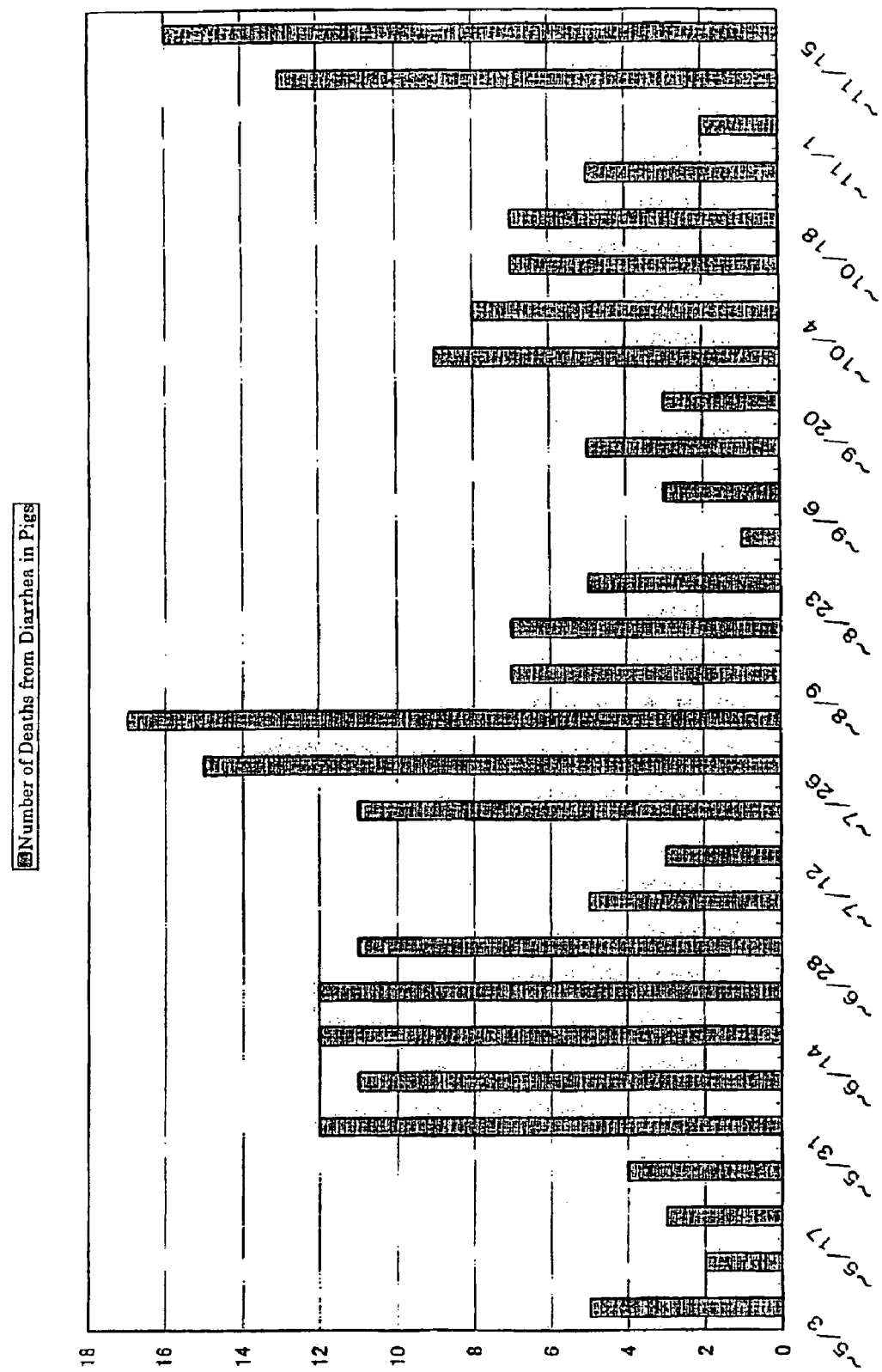

[Fig. 3]
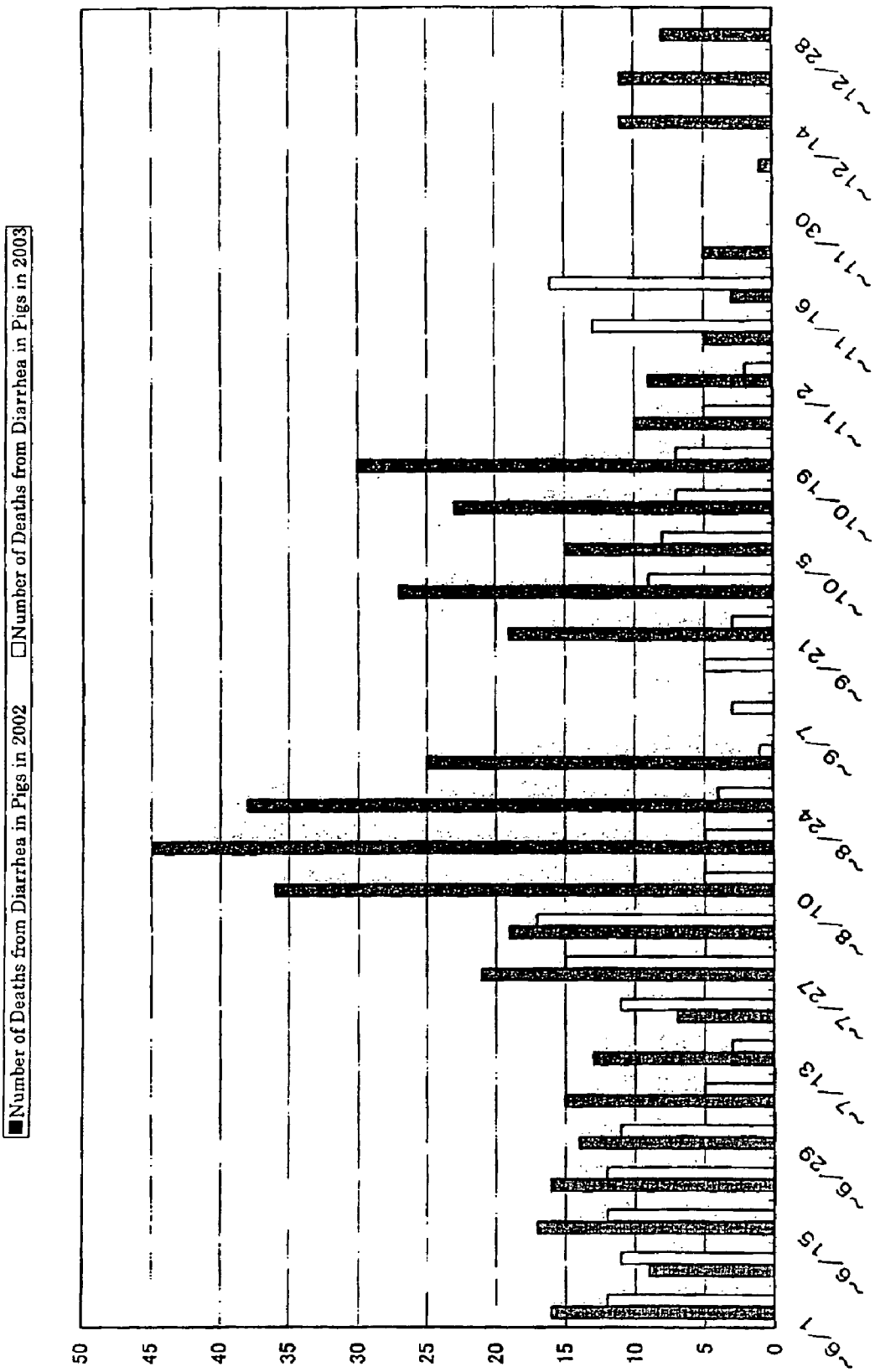

US 7,582,305 B2

ANTIDIARRHEAL AGENT FOR LIVESTOCK AND POULTRY

INCORPORATION BY REFERENCE

This application is a continuation-in-part application of international patent application Serial No. PCT/JP2005/004572 filed Mar. 15, 2005, and published as WO 2005/087240 on Sep. 22, 2005, which claims priority to Japanese patent application Serial No. JP 2004-075429 filed Mar. 16, 2004.

The foregoing applications, and all documents cited therein or during their prosecution ("appln cited documents") aid all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to an antidiarrheal agent for suppressing diarrhea which is caused by bacterial infection widely spread among livestock and poultry or by intestinal hypersensitivity. The antidiarrheal agent comprises killed bacteria of lactic acid bacteria *Enterococcus faecalis* EC-12 (FERM ABP-10284) or a treated product thereof as an active ingredient. The present invention also relates to a method for suppressing diarrhea, wherein the above agent is administered particularly to pigs.

BACKGROUND OF THE INVENTION

Conventionally, as therapeutic agents for livestock comprising lactic acid bacteria, agents for livestock comprising viable bacteria, *Lactobacillus acidophilus* and *Streptococcus faecalis* (see for example, Japanese Laid-Open Patent Application No. 51-106725) are known. These agents are for promoting growth or for preventing and treating diarrhea in livestock. Further, other known agents include mixed feed for livestock comprising, in ratio to 1 g of viable-bacterial agent such as bifidobacteria, sodium chloride at 2-12 g, potassium chloride at 1-10 g, sodium bicarbonate at 2-18 g, glucose at 10-80 g, and glycine at 5-30 g. This agent is used not only for curing diarrhea or a loose-stool symptom but also for obtaining glossier-looking hair and favorable growth in livestock such as pigs and cows (see for example, Japanese Laid-Open Patent Application No. 3-61452). Moreover, a dog food for preventing and treating dog-specific infections, comprising a treated product of bifidobacteria, lactic acid bacteria, or yeast is known (see for example, Japanese Laid-Open Patent Application No. 2001-309753).

Furthermore, the followings are known as applications of bacteria belonging to genus *Enterococcus* that are lactic acid bacteria and of a treated product thereof: an infection preventative against *candida* and the like (see for example, Japanese Laid-Open Patent Application No. 05-97689); and adjuvants (see for example, Japanese Laid-Open Patent Application No. 8-99887 and Japanese Laid-Open Patent Application No. 11-92389). The known applications still further include a method for producing lactic acid bacteria having an immuno-stimulating effect wherein *Enterococcus faecalis* EC-12 (FERM ABP-10284) is cultured by using a medium containing corn steep liquor and casein hydrolysate (see for example, Japanese Laid-Open Patent Application No. 2004-41099); and an immunoregulatory agents comprising killed bacteria of *Enterococcus faecalis* AD101 strain as a principal ingredient (see Japanese Laid-Open Patent Application No. 2001-48796) However, it was not known that *Enterococcus faecalis* EC-12 (FERM ABP-10284) has an extremely superior suppressive effect against diarrhea in livestock and poultry.

"Diarrhea" basically represents increased moisture content in feces, and is classified broadly according to the developmental mechanism of diarrhea into three groups: osmotic diarrhea; secretory diarrhea; and a diarrhea caused by abnormal transit time. Osmotic diarrhea is caused by increased osmotic pressure in the intestinal tract, which is attributed to substances that are not absorbed by the intestinal tract. Secretory diarrhea is caused by bacterial toxin, hormone, chemical substances and the like that accelerate secretion of water and electrolyte in the intestinal tract. Secretory diarrhea is wide in variety. Among secretory diarrheas, there are two types that are caused by bacteria: a type in which diarrhea is caused by bacterial toxin, and mucosal damage is not involved (for example, a certain kind of *Escherichia coli*); and the other type in which diarrhea is caused by mucosal damage induced by bacteria that have invaded into cells (for example, *Salmonella*). Fatty diarrhea and bile acid diarrhea based on malabsorption of fat or bile acid, are also a type of secretory diarrhea. In addition, diarrhea also occurs in inflammatory intestinal diseases as a result of increased permeability of intestinal wall. Among diarrheas with abnormal transit time in intestines, those attributed to lowering of speed include intestinal stenosis and blind loop syndrome such as diverticulosis. These diarrheas are caused by abnormal bacterial growth. Meanwhile, diarrheas attributed to enhancement of speed include irritable bowel syndrome and hyperthyroidism. These diarrheas are caused by increased intestinal motility.

In growing pigs, some weaning piglets and sows may develop dyspeptic diarrhea. Feeds for pigs being grown contain about 40-80% cereal which primarily comprises corns. Although starch is digested and absorbed in a pig's small intestines, the secretion of digestive enzyme and gastric acid is insufficient if a large amount of digesta comes at a time into the small intestines or in the case of a piglet around the weaning period or of a breast-feeding sow. In these cases, the starch cannot be completely absorbed and digested by the small intestines. Thus, the starch may come into the large intestines. Some bacteria of genus *Streptococcus*, a kind of lactic acid bacteria in the large intestines, quickly degrade starch and rapidly produce lactic acid. Some of such bacteria even multiply themselves. Thus, lactic acid abruptly increases in the large intestines. Consequently, an abrupt decrease in pH occurs. Such decrease kills or weakens other bacteria, resulting in abnormal large-intestinal flora. When such abnormal flora is generated, diarrhea occurs. At this moment, lactic acid as well as succinic acid, whose property is similar to that of lactic acid, are abundantly detected in the diarrheal stool.

As just described, diarrhea often occurs when an abnormal large-intestinal flora has been developed for various reasons. Further, mass accumulation of lactic acid adversely affects large-intestinal tissues. It not only damages the large-intestinal tissues and thus decreases thickness of the large intestines but also incurs possible secondary damage in which the large intestines become more susceptible to a pathogenic invasion as a result. Consequently, the large intestines become more susceptible to diarrhea-inducing pathogenic bacteria, pathogenic viruses and pathogenic protozoa, such as *Escherichia*

*coli, Clostridium perfringens, Brychispira hyodysenteriae, Lowsonia intracellaris, Salmonella* sp., rotavirus and coccidium.

Meanwhile, colibacillosis in pigs is broadly classified according to causative bacteria and the developmental mechanisms into *Escherichia coli* diarrhea, *Escherichia coli* enterotoxemia, and *Escherichia coli* septicemia. Diarrhea and septicemia frequently occur during the neonatal period. The principal cause of diarrhea is an infection of enterotoxigenic *Escherichia coli* which belongs to a specific serotype. Enterotoxemia is developed during the weaning period (4-12weeks old). The causative bacteria of Enterotoxemia are collectively referred to as Enterotoxemic *Escherichia coli* (ETEEC). ETEEC colonizes in the small intestines and produces toxin as a result. The absorbed toxin impairs the target tissue and thereby induces Toxemia. Edema disease (ED) is a typical *Escherichia coli* enterotoxemia. The causative bacteria of Edema disease (ED) belong to a specific serotype. These bacteria fall into the category of verotoxin-producing *Escherichia coli* (VTEC). Edema disease (ED) occurs sporadically in many cases, but at times, small-scale epidemics are provoked. On rare occasions, Edema disease attacks 2-3 week old suckling piglets or even adult pigs. Adult pigs follow more chronic courses than weaning piglets. Characteristically, Edema disease abruptly occurs in some pigs in the herd and ends after a short period of time (4-15 days). However, it may reappear repeatedly in the same farm. Although the attack rate of the disease is 10-40%, the death rate is as high as 50-90%. In many cases, Edema disease (ED) is caused by an infection with single-serotype bacteria. Meanwhile, it is sometimes caused by an infection with plural types of bacteria. The serotypes (0139, 0141) of causative bacteria of Edema disease (ED) are common in all countries. Experimentally, Edema disease is developed by orally administering $10^5 \times 0139$ bacteria for 3 days. It is known that a propagation usually occur via feces, aerosol or affected feed. It is also known that affected farms suffer from contamination over a long period of time ("Rinsho-to-Biseibutsu" Vol. 23, 843-849, 1996).

Of all livestock, pigs are recently in much demand particularly as edible meat. Among such pigs, piglets at the suckling period and around the weaning period or breast-feeding sows me attacked by Edema disease. Edema disease involves diarrhea which is caused by pathogenic *Escherichia coli*. Edema disease is often observed in weaned piglets. In an affected farm, 10-40% piglets are said to develop this disease.

Citation or identification of any document in this application is not an admission that such document is available as prior art to the present invention.

SUMMARY OF THE INVENTION

The object of the present invention is to provide a safe antidiarrheal agent and a method for suppressing diarrhea. By such agent and method, an efficient antidiarrheal effect is achieved without using antibiotics or synthetic antibacterial agents that have been conventionally used against infections in livestock and poultry. Moreover, antibiotic-resistant pathogenic infections can be prevented and treated by the antidiarrheal agent and method of the present invention.

The present inventors focused on diarrhea which attacks a high percentage of piglets around the weaning period during the growing period of pigs. As a result of a keen study on preventing and treating such diarrhea, the present inventors found out that administering killed bacteria of particular lactic acid bacteria, *Enterococcus faecalis* EC-12 (FERM ABP-10284) or a treated product thereof, significantly decreases diarrhea and Edema disease in piglets. Thus, the present inventors have completed the present invention.

The present invention relates to an antidiarrheal agent for livestock and poultry, which may comprise killed bacteria of *Enterococcus faecalis* EC-12 (FERM ABP-10284) or a treated product thereof as an active ingredient ("1"); the antidiarrheal agent for livestock and poultry according to "1", wherein the diarrhea factor may be attributable to pathogenic bacteria ("2"); the antidiarrheal agent for livestock and poultry according to "1" or "2", wherein the pathogenic bacteria may be are *Escherichia coli* ("3"); the antidiarrheal agent for livestock and poultry according to "3", wherein *Escherichia coli* may be *Escherichia coli* inducing Edema disease, or Enterotoxemic *Escherichia coli* ("4"); the antidiarrheal agent for livestock and poultry according to "1" or "2", wherein the pathogenic bacteria may be microorganisms belonging to genus *Clostridium* ("5"); the antidiarrheal agent for livestock and poultry according to "1", wherein the diarrhea factor may be coccidium protozoa ("6"); the antidiarrheal agent for livestock and poultry according to "1", wherein the diarrhea may be an irritable bowel diarrhea ("7"); and the antidiarrheal agent for livestock and poultry according to any one of "1" to "7", wherein the killed bacteria may be heat-killed bacteria ("8").

The present invention further relates to a method for suppressing diarrhea in livestock and poultry, wherein a composition comprising killed bacteria of *Enterococcus faecalis* EC-12 (FERM ABP-10284) or a treated product thereof as an active ingredient may be orally administered to livestock and poultry ("9"); the method for suppressing diarrhea in livestock and poultry according to "9", wherein the diarrhea factor may be attributable to pathogenic bacteria("10"); the method for suppressing diarrhea in livestock and poultry according to "10", wherein the pathogenic bacteria may be *Escherichia coli* ("11"); the method for suppressing diarrhea in livestock and poultry according to "11", wherein *Escherichia coli* may be *Escherichia coli* inducing Edema disease, or Enterotoxemic *Escherichia coli* ("12"); the method for suppressing diarrhea in livestock and poultry according to any one of "9" to "12", wherein the killed bacteria may be heat-killed bacteria ("13"); and the method for suppressing diarrhea in livestock and poultry according to any one of "9" to "13", wherein the antidiarrheal agent may be orally administered to a breast-feeding sow and a piglet around the weaning period ("14").

Accordingly, it is an object of the invention to not encompassed within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which:

FIG. 1 is a figure showing the weekly number of deaths from diarrhea in pigs (May 2002 to July 2002) since the administration of killed bacteria of EC-12 was started.

FIG. 2 is a figure showing the weekly number of deaths from diarrhea in pigs (May 2002 to November 2002) with changes in dosage since the administration of killed bacteria of EC-12 was started.

FIG. 3 is a figure showing the comparison of weekly number of deaths in weaned pigs between 2002 and 2003.

DETAILED DESCRIPTION

Diarrhea in livestock and poultry, particularly in pigs, is suppressed by orally administering the antidiarrheal agent for livestock aid poultry which comprises killed bacteria of *Enterococcus faecalis* EC-12 (FERM ABP-10284) or a treated product thereof as an active ingredient of the present invention. Moreover, administering the antidiarrheal agent substantially decreases the death rate attributed to diarrhea. Thus, an efficient antidiarrheal effect is achieved without using antibiotics or synthetic antibacterial agents that have been conventionally used against infections in livestock and poultry. Furthermore, antibiotic-resistant pathogenic infections can also be prevented and treated by such an antidiarrheal agent.

The antidiarrheal agent for livestock and poultry of the present invention is not particularly limited as long as it is a composition comprising killed bacteria of lactic acid bacteria, *Enterococcus faecalis* EC-12 (FERM ABP-10284) or a treated product thereof, as an active ingredient. Further, the method for suppressing diarrhea in livestock and poultry of the present invention is not particularly limited as long as it is a method for orally administering to livestock and poultry a composition comprising killed bacteria of lactic acid bacteria, *Enterococcus faecalis* EC-12 (FERM-10284) or a treated product thereof, as an active ingredient. The above infection preventative or composition can be used in any form, directly or as a formulation or the like.

Table 1 shows the mycological characteristics of *Enterococcus faecalis* EC-12 used in the present invention. A method for culturing *Enterococcus faecalis* EC-12 includes conventionally known methods for culturing lactic acid bacteria, and is not limited particularly. Such a method, however, can be exemplified by a method for obtaining culture solution with about $10^7$-$10^{10}$/ml, preferably about $10^8$-$10^{10}$/ml viable bacteria, by culturing with a medium for culturing lactic acid bacteria for 5-120 hours, preferably for 16-28 hours at 37° C., while maintaining the culture pH near the neutral point. Further, *Enterococcus faecalis* EC-12 is deposited as "FERM ABP-10284" with the International Patent Organism Depositary, National Institute of Advanced Industrial Science and Technology (Tsukuba Central 6, 1-1, Higashi 1-chome, Tsukuba-shi, Ibaraki-ken, 305-8566 Japan) on Feb. 25, 2005. Also, 16SrDNA of *Enterococcus faecalis* EC-12 is registered as "AB15482" with the National Institute of Genetics.

TABLE 1

| Deposit Number | IFO16803 |
|---|---|
| Strain | *E. faecalis* EC-12 strain |
| shape of cells | Globular |
| gram staining property | + |
| Catalase | − |
| NaCl (6.5%) proliferation | + |
| proliferation in a pH 9.6 medium | + |
| proliferation in a bile acid medium (4%) | + |
| Arabinose | − |
| Melibiose | − |
| Sorbose | − |
| Melezitose | + |
| Sorbitol | + |

In the present invention, *Enterococcus faecalis* EC-12 should be used as killed bacteria or a treated product thereof. Examples of such killed bacteria include a killed-bacterial suspension or a dried product thereof that can be obtained by the steps of: culturing and harvesting lactic acid bacteria by a common method; washing and dehydrating by centrifugation; repeating the operation of washing and dehydration according to need, and suspending the resultants in distilled water, normal saline solution or the like; heating the suspension, for example, at 80-115° C. for 30 min to 3 sec. Other examples include a killed-bacterial suspension or a dried product thereof obtained by irradiating the above-mentioned killed-bacterial suspension with gamma ray or neutron ray. The means for drying the killed-bacterial suspension is not specifically limited as long as it is a commonly known drying means. Examples of such a drying means include spray drying or lyophilization. Depending on circumstances, treatment with enzyme or surfactant, or processing by grinding and crushing can be conducted before or after sterilization treatment by heating and the like, or before or after drying treatment. The resultants of these treatments are also within the scope of killed bacteria or a treated product thereof of the present invention.

When using the above-mentioned antidiarrheal agent or composition as a formulation, it can be compounded with a carrier such as starch, lactose and soy protein; or additives such as excipient, binding agent, disintegrator, lubricant, stabilizer and suspending agent, to be formulated into powder, tablet, granules, capsules, syrup or the like by a common method. The formulation can be administered directly or can be fed by mixing it with feed or the like.

In the present invention, examples of livestock or poultry which represent the target of diarrheal suppression include livestock such as, but not limited to, cows, pigs, horses, sheep, goats; and poultry such as chickens, ducks and ostriches. The diarrheal suppression can be applied to livestock or poultry of any age in days or years, including those in the breast-feeding period and the suckling period. Particularly in growing pigs, it is preferable to orally administer the antidiarrheal agent to breast-feeding sows and piglets around the weaning period, from a standpoint of preventing Edema-disease infection. As mentioned above, pig-diarrhea often occurs particularly in weaned piglets and suckling piglets. As a cause of occurrence, farming environment factors such as the structure of a farrowing house or weaning house where the pigs are kept; seasonal factors such as rainy season when *Escherichia coli* easily generate as well as hot summer or cold winter weaning piglets' immune system compromises; suckling factors such as wrong weaning method resulting in indigestion and the like; growing factors such as malnutrition; hereditary factors and the like, are believed to be involved in a complicated way. The principal symptoms are characterized by palpebral edema (reddish inflammation), significant mesenteric lymph node swelling, and diarrhea as well as neurological symptoms.

The antidiarrheal agent of the present invention is useful not only for treating but also for preventing diarrhea. Preferably, the antidiarrheal agent may be administered to livestock or poultry when, for example, the resistance is lowered; diarrhea is widespread in the neighborhood; livestock or poultry are pregnant, breast-feeding, or suckling and the like; and needless to say when a diarrheal symptom is developed. Further, diarrhea can be preferably exemplified by irritable bowel diarrhea or diarrhea caused by pathogenic bacteria or coccidium protozoa. Furthermore, the above pathogenic bacteria can be specifically exemplified by *Escherichia coli*, particularly those which cause Edema disease, or by Enterotoxemeic *Escherichia coli* as well as microorganisms such as *Clostridium perfringens* which belong to genus *Clostridium*.

The dosage and the number of doses of antidiarrheal agent of the present invention and of the composition used in the method for suppressing diarrhea of the present invention can be determined as desired, according to the type, body weight, diarrheal symptom, recovery condition and the like of livestock and poultry. Meanwhile, in the case of piglets for example, it is preferable to administer to weaned piglets 0.1-200 mg/day per kg of body weight, preferably 20-100 mg/day per kg of body weight of killed bacteria of *Enterococcus faecalis* EC-12 or a treated product thereof by mixing it with normal feed. The dosing period may vary depending on the health condition and surroundings of piglets, while appropriate period is from 21 to 42 days old, more preferably from 5 to about 70 days old.

The invention will now be further described by way of the following non-limiting examples which further illustrate the invention, and are not intended, nor should they be interpreted to, limit the scope of the invention.

EXAMPLES

Example 1

Culturing and Preparation of Bacteria

*Enterococcus faecalis* EC-12 (FERM ABP-10284) was cultured in a Rogosa medium at 37° C. for 24 hours. The preculture solution was inoculated in a amount of 0.1 (v/v) % to a liquid medium which contains 4% yeast extract, 3% polypepton, and 10% lactose. By adjusting the pH to 6.8-7.0 with sodium hydroxide solution by using a pH stat, a neutralizing culture was conducted at 37° C. for 22-24 hours.

After the culturing was completed, the bacteria were separated with a continuous centrifuge and collected. Then, water was added to dilute up to the original liquid level, and the bacteria were separated again with a continuous centrifuge and then collected. This operation was repeated 4 times to wash the bacteria. Subsequently, the washed bacteria were suspended in an appropriate amount of water. The bacteria were then sterilized at 100° C. for 30 min and dried by using a spray drier to prepare powder of heat-killed bacteria.

Example 2

Identification of Pathogenesis Factors and Clinical Scores

1. Test Feed/Test Animals/Growing Method

Dried killed bacteria (hereinafter referred to as "EC-12") obtained in Example 1 was diluted 10-fold with flour to make a premix in advance. Thereafter, the premix was added to basic feed SDS No. 1 (without antibacterial agent or live-bacterial agent, Nippon Formula Feed Manufacturing Co., Ltd.) so that the feed to be used contains 0.05% EC-12. As a control feed, the basic feed which was added 0.5% commercially available flour was used. As for test animals, the subjects were 31 (4 broods) suckling piglets (LWD-strain three-way-crossed pigs) with diarrheal symptom. The suckling piglets were grown in pig farms where diarrhea had frequently occurred in suckling and weaning piglets. The suckling piglets were 18-24 days old and were grown with sows in the farrowing stall. The piglets fed only on breast-milk. The group with EC-12 administration was weaned 4 or 8 days after starting the test, while the control group without administration was weaned 2 days after starting the test. Meanwhile, no agent had been administered to the sows and the test piglets since farrowing.

2.2. The Test Scheme

Before administration, feces were collected with swabs from all the test pigs. The feces were then examined quantitatively on the positive ratio for pathogenesis factors. Subsequently, EC-12-supplemented feed was given to 21 test pigs (3 broods), while the EC-12-free feed (control) was given to the 10 remaining pigs (1 brood) for 14 days. During that time, feces were collected with swabs from all the pigs on day 7 after starting the administration. Then, the administration was continued for 7 days to observe the process. Specifically, tests were conducted for identifying pathogenesis factors and for obtaining mean clinical scores as well as body weight values.

2.3. Identification of Pathogenesis Factors

The detection of pathogenic bacteria was conducted on days 0 and 7 after starting the administration of *Clostridium perfringens* (1), *Salmonella* sp. (2), and hemolytic *Escherichia coli* (3). These bacteria are infectious particularly for piglets in the suckling period. Table 2 shows the test results for pathogenesis factors in the feces. The feces were collected at the time of observation on day 14 after starting the administration. The feces were tested for *Brychispira hyodysenteriae, Lowsonia intracellaris*, Rotavirus and coccidium, the results of all cases being negative.

TABLE 2

| Test Group ID No. | Hemolytic *E. coli* | | *Clostridium perfringen* | | *Salmonella* Spp. | |
|---|---|---|---|---|---|---|
| | 0 d | 7 d | 0 d | 7 d | 0 d | 7 d |
| Positive ratio (%) of control group without administration | 0 | 90* | 10 | 0 | 0 | 0 |

TABLE 2-continued

| Test Group ID No. | Hemolytic E. coli 0 d | 7 d | Clostridium perfringen 0 d | 7 d | Salmonella Spp. 0 d | 7 d |
|---|---|---|---|---|---|---|
| Positive ratio (%) of group with EC-12 administration | 5 | 0 | 57 | 0* | 0 | 0 |
| p-value in Fisher's exact probability test | 0.68 | <0.001 | 0.02 | N.C. | N.C. | N.C. |

*Wilcoxon signed rank sum test was conducted. This test showed a significant difference between the values before and after the administration.

As a result, the positive ratio for hemolytic *Escherichia coli* in the control group without administration was 0% (0/10 cases) on day 0 after starting the test. The ratio was 90% (9/10 cases) on day 7 after starting the test. Wilcoxon signed rank sum test was conducted. The test showed a significant difference between the results of day 0 and day 7 after starting the test. In the group with EC-12 administration, the ratio was 5% (1/21 cases) on day 0 after starting the test, while the ratio was 0% (0/21 cases) on day 7 after starting the test. Fisher's exact probability test was conducted at the time of each observation. On day 7 after starting the test, this test showed a significant difference between the results for control group without administration and the group with EC-12 administration. Further, the positive ratio for *Clostridium perfringens* in the control group without administration was 10% (1/10 cases) on day 0 after starting the test, while the ratio was 0% (0/10 cases) on day 7 after starting the test. In the group with EC-12 administration, the ratio was 57% (13/21 cases) on day 0 after starting the test, and 0% (0/21 cases) on day 7 after starting the test. Wilcoxon's signed rank sum test was conducted. This test showed a significant difference between the results for day 0 and day 7 after starting the test. Fisher's exact probability test was conducted at the time of each observation. On day 0 after starting the test, this test showed a significant difference between the results for control group without administration and the group with EC-12 administration. Meanwhile, no salmonella was detected throughout the test period.

2.4. Mean Clinical Score

On days 0, 1, 2, 3, 4, 7, 10 and 14 after starting the administration, feces condition, vitality, coat-hair and appetite were observed and recorded to obtain the comprehensive clinical scores. The results are shown in Table 3.

TABLE 3

| Observation Items | Tested group | Number of Test Animals | 0 | 1 | 2 | 3 | 4 | 7 | 10 | 14 | Totals during administration period 1-14 d |
|---|---|---|---|---|---|---|---|---|---|---|---|
| Feces condition | Control group without administration | 10 | 1.8 | 1.4 | 0.9 | 1.0 | 1.2 | 1.9 | 1.4 | 1.1 | 8.9 |
| | Group with EC-12 Administration | 21 | 1.5 | 0.7 | 0.5 | 0.6 | 0.6 | 0.5 | 0.4 | 0.8 | 4.0 |
| | p-value in Mann-Whitney test | | 0.15 | 0.02 | 0.03 | 0.10 | 0.04 | <0.001 | <0.001 | 0.2 | <0.001 |
| Vitality | Control group without administration | 10 | 0.0 | 0.0 | 0.0 | 0.0 | 0.0 | 0.0 | 0.0 | 0.2 | 0.2 |
| | Group with EC-12 Administration | 21 | 0.0 | 0.0 | 0.0 | 0.0 | 0.0 | 0.0 | 0.0 | 0.0 | 0.0 |
| | p-value in Mann-Whitney test | | N.C | N.C | N.C | N.C | N.C | N.C | N.C | 0.04 | 0.04 |
| Coat-hair | Control group without administration | 10 | 0.1 | 0.0 | 0.0 | 0.0 | 0.0 | 0.0 | 0.4 | 0.7 | 1.1 |
| | Group with EC-12 Administration | 21 | 0.0 | 0.0 | 0.0 | 0.0 | 0.0 | 0.0 | 0.0 | 0.0 | 0.0 |
| | p-value in Mann-Whitney test | | 0.15 | N.C | N.C | N.C | N.C | N.C | 0.002 | <0.001 | <0.001 |
| Appetite | Control group without administration | 10 | 0.0 | 0.0 | 0.0 | 0.0 | 0.0 | 0.0 | 0.0 | 0.1 | 0.1 |
| | Group with EC-12 Administration | 21 | 0.0 | 0.0 | 0.0 | 0.0 | 0.0 | 0.0 | 0.0 | 0.0 | 0.0 |
| | p-value in Mann-Whitney test | | N.C | N.C | N.C | N.C | N.C | N.C | N.C | 0.59 | 0.59 |
| Comprehensive Clinical Score | Control group without administration | 10 | 1.9 | 1.4 | 0.9 | 1.0 | 1.2 | 1.9 | 1.8 | 2.1 | 10.3 |
| | Group with EC-12 Administration | 21 | 1.5 | 0.7 | 0.5 | 0.6 | 0.6 | 0.5 | 0.4 | 0.9 | 4.1 |
| | p-value in Mann-Whitney test | | 0.09 | 0.02 | 0.03 | 0.1 | 0.04 | <0.001 | <0.001 | 0.008 | <0.001 |

Regarding the feces condition scores, the feces condition score for the control group without administration was 1.8 on day 0, 1.4 on day 1, 0.9 on day 2, 1.0 on day 3, 1.2 on day 4, 1.9 on day 7, 1.4 on day 10 and 1.1 on day 14 after starting the test. The total score from day 1 to day 14 after starting test (during the EC-12 administration period) was 8.9. For the group with EC-12 administration, the score was 1.5 on day 0, 0.7 on day 1, 0.5 on day 2, 0.6 on days 3 and 4, 0.5 on day 7, 0.4 on day 10 and 0.8 on day 14 after starting the test. The total score from day 1 to day 14 after starting the test (during the EC-12 administration period) was 4.0. Mann-Whitney test was conducted at the time of each observation. This test showed significant differences among the results for days 1, 2, 4, 7 and 10 after starting the test. Comparing the total scores during the EC-12 administration period also showed significant differences.

2.5. Body Weight Measurement

Body weights were measured on days 0, 7, and 14 after starting the test. Table 4 shows the results of the body weight measurement. It also shows changes in weight gain during the test period.

TABLE 4

Results of body weight measurement and weight gain during the test-period (Kg)

| Test group | Number of Test Animals | | Days after starting the test | | | Weight gain during the test period | | |
|---|---|---|---|---|---|---|---|---|
| | | | 0 d | 7 d | 14 d | 0-7 d | 7-14 d | 0-14 d |
| Control group without Administration | 10 | Mean Standard Deviation | 5.2 1.1 | 5.9 1.3 | 6.8 1.3 | 0.7 0.3 | 0.9 0.4 | 1.6 0.6 |
| Group with EC-12 Administration | 21 | Mean Standard Deviation | 5.3 1.1 | 6.3 1.2 | 6.6 1.3 | 1.0 0.4 | 0.3 0.5 | 1.3 0.6 |
| p-value in t-test | | | 0.94 | 0.22 | 0.87 | <0.001 | 0.01 | 0.65 |

Regarding the vitality scores, the mean vitality score for the control group without administration was 0.0 from day 0 to day 10, and 0.2 on day 14 after starting the test. For the group with EC-12 administration, the vitality scores were all 0.0 throughout the test period. Mann-Whitney test was conducted on day 14 after starting the test. This test showed a significant difference.

Regarding the coat-hair scores, the mean coat-hair score for the control group without administration was 0.1 on day 0, 0.0 from day 1 to day 7, 0.4 on day 10 and 0.7 on day 14 after starting the test. The total score during the EC-12 administration period was 1.1. For the group with EC-12 administration, the coat-hair scores were all 0.0 during the test period. Mann-Whitney test was conducted at the time of each observation. This test showed a significant difference between the results for day 10 and 14 after starting the test. Comparing the total scores during the EC-12 administration period also showed significant differences.

Regarding the appetite score, the mean appetite score for the control group without administration was 0.0 from day 0 to day 10, and 0.1 on day 14 after starting the test. For the group with EC-12 administration, the appetite scores were all 0.0 during the test period. Mann-Whitney test was conducted on day 14 after starting the test. This test showed no significant difference.

Regarding the comprehensive clinical scores, the mean comprehensive clinical score for the control group without administration was 1.9 on day 0, 1.4 on day 1, 0.9 on day 2, 1.0 on day 3, 1.2 on day 4, 1.9 on day 7, 1.8 on day 10 and 2.1 on day 14 after starting the test. The total score during the EC-12 administration period was 10.3. For the group with EC-12 administration, the score was 1.5 on day 0, 0.7 on day 1, 0.5 on day 2, 0.6 on days 3 and 4, 0.5 on day 7, 0.4 on day 10 and 0.9 on day 14. The total score during the EC-12 administration period was 4.1. Mann-Whitney test was conducted at the time of each observation. This test showed significant differences among the results for days 1, 2, 4, 7, 10 and 14. Comparing the total scores during the EC-12 administration period also showed significant differences.

As a result, the mean weight for the control group without administration was 5.2 kg on day 0, 5.9 kg on day 7 and 6.8 kg on day 14 after starting the test. Meanwhile, for the group with EC-12 administration, the mean weight was 5.3 kg on day 0, 6.3 kg on day 7 and 6.6 kg on day 14 after starting the test. The t-test results did not show any significant difference at any point of time. Further, for the control group without administration, the mean weight gain during the test period was 0.7 kg for days 0-7, 0.9 kg for days 7-14 and 1.6 kg for days 0-14 after starting the test. Meanwhile, for the group with EC-12 administration, the mean weight gain during the test period was 1.0 kg for days 0-7, 0.3 kg for days 7-14 and 1.3 kg for days 0-14 after starting the test. In the t-test results, the value for the group with EC-12 administration was greater for days 0-7 than the other group, while the value for the control group without administration was greater for days 7-14 than the other group, respectively.

2.6. Conclusion

From day 1 after starting EC-12 administration, the feces condition significantly improved. This tendency was observed until the end of the test. On day 14 after starting the test, pigs in one chamber (weaned 8 days after starting the test) with EC-12 administration sporadically exhibited recurrence of diarrhea. Meanwhile, pigs in other two chambers exhibited no serious recurrence. As for other clinical scores, some pigs in the control group without administration exhibited vitality loss, dull-looking coat-hair and poor appetite due to continuous diarrhea. The group with EC-12 administration, however, exhibited none of the above symptoms throughout the test period. In the test for pathogenesis factor in feces, 9 out of 10 pigs in the control group without administration tested positive for hemolytic *Escherichia coli* on day 7 after starting the test. Meanwhile, all the pigs in the group with EC-12 administration tested negative. Furthermore, 13 out of 21 pigs in the group with EC-12 administration, which were tested positive for *Clostridium perfringens* on day 0 after starting the test, all turned negative by day 7 after starting the test. These results suggested the possibility that administering EC-12 to suckling piglets suppresses diarrheas that are caused by pathogenic *Escherichia coli* and *Clostridium perfringens*. Further, no abnormality attributable to EC-12 administration was found during the test. Thus, safety of EC-12 administration to pigs was confirmed.

Example 3

Decrease in the Number of Deaths in Piglets 3.1. Test Scheme

The test farm raises 400 sows under a coherent management. It has open-type pig-houses as farrowing houses as well as windless pig-houses as weaning houses. The test farm implements all-in/all-out system. From the start of feeding until day 7 after weaning, piglets of 5-33 days old were administered EC-12 by mixing it in the feed. Other test conditions were the same as those in Example 2. The administration of 100 mg per kg of body weight of EC-12 was started on Jun. 22, 2002. The administration was continued until Jul. 18, 2002. The dosage was reduced by half from Jul. 19, 2002 and 50 mg per kg of body weight was administered until Aug. 2, 2002. Then from Aug. 3, 2002, the dosage was returned to the original amount and 100 mg per kg of body weight was administered until Sep. 27, 2002. Subsequently, the dosage was doubled and 200 mg per kg of body weight was administered until December 2003.

3.2. Administration Effect

As shown in FIG. 1, the incidence of diarrhea lowered from the week after the start of the administration that was Jun. 22, 2002. Moreover, the number of deaths attributed to diarrhea decreased to less than half. Further, as shown in FIG. 1, represents the ages in days of dead piglets, the number of which is shown outside the figure section, along the vertical axes on the right-hand side. Since the ages in days at death ranged from about 35 to 45 days old, it has been revealed that administration should be preferably started from younger age in days than 35-45 days old.

The dosage was reduced by half from Jul. 19, 2002 and 50 mg per kg of body weight was administered for 2 weeks until Aug. 2, 2002. As a result, the number of deaths increased as shown in FIG. 2. It was considered that this result may have been brought by the environmental effect of the farrowing house and the weaning house. However, it was believed that the increase in number of deaths was further related to the dosage reduced by half. Subsequently, the dose was returned to the original amount from August 3, that is, 100 mg per kg of body weight was administered until the last week of September. Consequently, the number of deaths decreased to less than ½-⅓. The number of death was as small as one during the week ending September 6, as shown in FIG. 2.

Since the number of deaths began to increase from the last week of September, the dosage was doubled, that is, 200 mg per kg of body weight was administered. Consequently, as shown in FIG. 2, the number of deaths gradually decreased to the extent of two during the week ending November 8. Throughout the following two weeks, the number of deaths increased. The reason for this was not obvious, but it was believed that the farrowing-house environment was responsible. The old farrowing house was a house wherein the temperature control was bad that the temperature inside the house was almost the same as outside temperature. FIG. 3 shows the numbers of deaths in 2003 along with the number of deaths in the same week of 2002. It is obvious from the number of deaths shown in FIG. 3 that the numbers in 2003, wherein EC-12 of the present invention was administered, are obviously smaller compared with those in 2002.

The invention is further described by the following numbered paragraphs:

1. An antidiarrheal agent for livestock and poultry, which comprises killed bacteria of *Enterococcus faecalis* EC-12 (FERM ABP-10284) or a treated product thereof as an active ingredient.

2. The antidiarrheal agent for livestock and poultry according to paragraph 1, wherein the diarrhea factor is attributable to pathogenic bacteria.

3. The antidiarrheal agent for livestock and poultry according to paragraph 1 or 2, wherein the pathogenic bacteria are *Escherichia coli*.

4. The antidiarrheal agent for livestock and poultry according to paragraph 3, wherein *Escherichia coli* is *Escherichia coli* inducing Edema disease, or Enterotoxemic *Escherichia coli*.

5. The antidiarrheal agent for livestock and poultry according to paragraph 1 or 2, wherein the pathogenic bacteria are microorganisms belonging to genus *Clostridium*.

6. The antidiarrheal agent for livestock and poultry according to paragraph 1, wherein the diarrhea factor is coccidium protozoa.

7. The antidiarrheal agent for livestock and poultry according to paragraph 1, wherein the diarrhea is an irritable bowel diarrhea.

8. The antidiarrheal agent for livestock and poultry according to any one of paragraphs 1 to 7, wherein the killed bacteria are heat-killed bacteria.

9. A method for suppressing diarrhea in livestock and poultry, wherein a composition comprising killed bacteria of *Enterococcus faecalis* EC-12 (FERM ABP-10284) or a treated product thereof as an active ingredient is orally administered to livestock and poultry.

10. The method for suppressing diarrhea in livestock and poultry according to paragraph 9, wherein the diarrhea factor is attributable to pathogenic bacteria.

11. The method for suppressing diarrhea in livestock and poultry according to paragraph 10, wherein the pathogenic bacteria are *Escherichia coli*.

12. The method for suppressing diarrhea in livestock and poultry according to paragraph 11, wherein *Escherichia coli* is *Escherichia coli* inducing Edema disease, or Enterotoxemic *Escherichia coli*.

13. The method for suppressing diarrhea in livestock and poultry according to any one of paragraphs 9 to 12, wherein the killed bacteria are heat-killed bacteria.

14. The method for suppressing diarrhea in livestock and poultry according to any one of paragraphs 9 to 13, wherein the antidiarrheal agent is orally administered to a breast-feeding sow and a piglet around the weaning period.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for suppressing diarrhea in pigs, wherein a composition comprising killed bacteria of *Enterococcus faecalis* EC-12 (FERM ABP-10284) as an active ingredient is orally administered to pigs.

2. The method for suppressing diarrhea in pigs of claim 1, wherein the diarrhea is attributable to pathogenic bacteria.

3. The method for suppressing diarrhea in pigs of claim 2, wherein the pathogenic bacteria are *Escherichia coli*.

4. The method for suppressing diarrhea in pigs of claim 3, wherein *Escherichia coli* is *Escherichia coli* inducing Edema disease, or Enterotoxemic *Escherichia coli*.

5. The method for suppressing diarrhea in pigs of claim 1, wherein the killed bacteria are heat-killed bacteria.

6. The method for suppressing diarrhea in pigs of claim 1, wherein the composition is orally administered to a breast-feeding sow or a piglet around the weaning period.

* * * * *

UNITED STATES PATENT AND TRADEMARK OFFICE
CERTIFICATE OF CORRECTION

PATENT NO. : 7,582,305 B2  
APPLICATION NO. : 11/522161  
DATED : September 1, 2009  
INVENTOR(S) : Kazunari Ushida et al.

Page 1 of 1

It is certified that error appears in the above-identified patent and that said Letters Patent is hereby corrected as shown below:

Title page, Item (74), "Fromer" should be changed to --Frommer--.

Signed and Sealed this

Tenth Day of November, 2009

David J. Kappos  
*Director of the United States Patent and Trademark Office*